United States Patent
Mori

(10) Patent No.: US 7,956,089 B2
(45) Date of Patent: Jun. 7, 2011

(54) CYCLOPROPANECARBOXYLATE AND PEST CONTROLLING COMPOSITION CONTAINING THE SAME

(75) Inventor: Tatsuya Mori, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/809,106

(22) PCT Filed: Dec. 19, 2008

(86) PCT No.: PCT/JP2008/073890
§ 371 (c)(1),
(2), (4) Date: Sep. 13, 2010

(87) PCT Pub. No.: WO2009/082018
PCT Pub. Date: Jul. 2, 2009

(65) Prior Publication Data
US 2010/0331408 A1 Dec. 30, 2010

(30) Foreign Application Priority Data
Dec. 21, 2007 (JP) .................. 2007-329898

(51) Int. Cl.
*A01N 53/00* (2006.01)
*C07C 19/08* (2006.01)
*C07C 69/74* (2006.01)
(52) U.S. Cl. .................. 514/531; 570/127; 560/124
(58) Field of Classification Search .................. 514/531; 570/127; 560/124
See application file for complete search history.

(56) References Cited

FOREIGN PATENT DOCUMENTS

| EP | 0196156 A1 | | 10/1986 |
|---|---|---|---|
| GB | 2097384 | * | 2/1982 |
| JP | 07-017916 A | | 1/1995 |
| JP | 2001-302590 A | | 10/2001 |

OTHER PUBLICATIONS

A.W. Farnham et al., "The pyrethrins and related compounds Part XL—Structure-Activity Relationships of Pyrethroidal esters with Acyclic Side Chains in the Alcohol Component against Resistant Strains of Housefly (musca domestica)", Pestic. Sci., vol. 44. pp. 277-281, (1995).

International Preliminary Report on Patentability issued on Jun. 22, 2010 in International Application No. PCT/JP2008/073890.

* cited by examiner

*Primary Examiner* — Jafar Parsa
(74) *Attorney, Agent, or Firm* — Panitch Schwarze Belisario & Nadel LLP

(57) ABSTRACT

There is provided a novel cyclopropanecarboxylate compound having an excellent pest controlling effect represented by the formula (1):

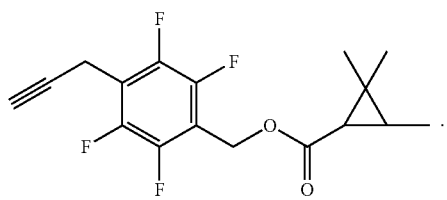

3 Claims, No Drawings

CYCLOPROPANECARBOXYLATE AND PEST CONTROLLING COMPOSITION CONTAINING THE SAME

CROSS-REFERENCE TO RELATED APPLICATION

This application is a section 371 of International Application No. PCT/JP2008/073890, filed Dec. 19, 2008, which was published in the English language on Jul. 2, 2009 under International Publication No. WO 2009/082018 A1 and the disclosure of which is incorporated herein by reference.

TECHNICAL FIELD

The present invention relates to a certain cyclopropanecarboxylate and a pest controlling composition containing the same.

BACKGROUND ART

Heretofore, various compounds have been synthesized for controlling pests. For example, a certain kind of cyclopropanecarboxylate derivatives was described in JP-A 7-17916 and JP-A 2001-302590. However, the pest controlling effect of the cyclopropanecarboxylate derivatives described in JP-A 7-17916 and JP-A 2001-302590 was not high enough.

DISCLOSURE OF THE INVENTION

An object of the present invention is to provide a novel compound having an excellent pest controlling effect.

The present inventors have intensively studied and have found that an ester compound represented by the formula (1) shown hereinafter has an excellent pest controlling effect. Thus, the present invention has been completed.

That is, the present invention provides:

[1] A cyclopropanecarboxylate represented by the formula (1):

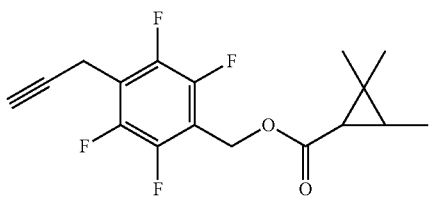

(hereinafter, sometimes, referred to as the present compound);

[2] A pest controlling composition, which comprises the cyclopropanecarboxylate according to [1] as an active ingredient; and

[3] A pest controlling method, which comprises applying an effective amount of the cyclopropanecarboxylate according to [1] to a pest or a habitat of the pest.

Since the present compound has an excellent pest controlling effect, it is useful as an active ingredient of a pest controlling composition.

BEST MODE FOR CARRYING OUT THE INVENTION

In the present compound, there exist two asymmetric carbon atoms on the cyclopropane ring. The present invention includes all of the active isomers and mixtures thereof in given ratios.

Examples of the present compound include the following compounds:

A compound of the formula (1), wherein the absolute configuration at the 1-position on the cyclopropane ring is R-configuration;

A compound of the formula (1), wherein the relative configuration of substituents at the 1-position and the 3-position on the cyclopropane ring is trans-configuration;

A compound of the formula (1), wherein the relative configuration of substituents at the 1-position and the 3-position on the cyclopropane ring is cis-configuration;

A compound of the formula (1), wherein the absolute configuration at the 1-position on the cyclopropane ring is R-configuration, and the relative configuration of substituents at the 1-position and the 3-position on the cyclopropane ring is trans-configuration; and A compound of the formula (1), wherein the absolute configuration at the 1-position on the cyclopropane ring is R-configuration, and the relative configuration of substituents at the 1-position and the 3-position on the cyclopropane ring is cis-configuration;

When the present compound exists as a mixture of isomers, examples of the isomer mixture include the following mixtures:

An isomer mixture comprising abundance of a compound of the formula (1) wherein the absolute configuration at the 1-position on the cyclopropane ring is R-configuration and the relative configuration of substituents at the 1-position and the 3-position on the cyclopropane ring is trans-configuration;

An isomer mixture comprising 80% or more of a compound of the formula (1) wherein the absolute configuration at the 1-position on the cyclopropane ring is R-configuration and the relative configuration of substituents at the 1-position and at the 3-position on the cyclopropane ring is trans-configuration; and An isomer mixture comprising 90% or more of a compound of the formula (1) wherein the absolute configuration at the 1-position on the cyclopropane ring is R-configuration and the relative configuration of substituents at the 1-position and the 3-position on the cyclopropane ring is trans-configuration.

Herein, an indicated proportion in each isomer mixture means the content of an isomer in the isomer mixture.

The present compound can be produced, for example, by production processes as described below.

Production Process 1

A process comprising a reaction of a 4-(2-propynyl)-2,3,5,6-tetrafluorobenzyl alcohol compound of the formula (2):

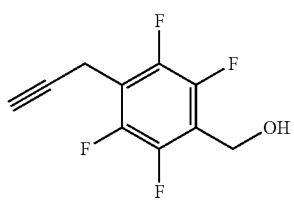

with carboxylic acid of the formula (3):

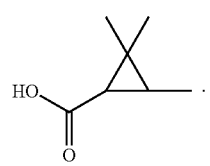

The reaction is usually carried out in the presence of a condensing agent and a base, or in the presence of an acid catalyst. The reaction is usually carried out in a solvent.

Examples of the condensing agent include dicyclohexylcarbodiimide and 1-ethyl-3-(3-dimethylaminopropyl)carbodiimide hydrochloride. Examples of the base include organic bases such as triethylamine, pyridine, N,N-diethylaniline, 4-dimethylaminopyridine and diisopropylethylamine. Examples of the acid catalyst include inorganic acids such as sulfuric acid, and sulfonic acids such as paratoluenesulfonic acid and methanesulfonic acid. The solvent to be used may be an inert solvent in the reaction, and examples thereof include hydrocarbons such as toluene and hexane; ethers such as diethyl ether and tetrahydrofuran; halogenated hydrocarbons such as chloroform, dichloromethane and 1,2-dichloroethane; and their mixtures.

The reaction time of the reaction is usually from an instant to 72 hours, and the reaction temperature is usually in the range from −20° C. to 100° C.

The amount of the alcohol compound of the formula (2) to be used in the reaction is theoretically 1 mol per 1 mol of the carboxylic acid of the formula (3), and however, it can be appropriately selected in the range from 0.5 to 1.5 mol per 1 mol of the carboxylic acid of the formula (3).

When the reaction is carried out in the presence of a condensing agent and a base, the amount of the condensing agent to be used in the reaction is usually 1 mol per 1 mol of the carboxylic acid of the formula (3), and however, it can be appropriately changed according to the reaction conditions. The amount of the base to be used in the reaction is usually in the range from 0.1 to 1 mol per 1 mol of the carboxylic acid of the formula (3).

When the reaction is carried out in the presence of an acid catalyst, the amount of the acid catalyst to be used in the reaction is usually in the range from 0.01 to 20 mol per 1 mol of the carboxylic acid of the formula (3), and however, it can be appropriately changed according to the reaction conditions.

After completion of the reaction, the present compound can be isolated by subjecting a reaction mixture to conventional after-treatment operations such as pouring into water, followed by extraction with an organic solvent and further concentration. If necessary, the present compound thus isolated can be purified by subjecting to a purification operation such as chromatography and distillation.

Production Process 2

A process comprising a reaction of the alcohol compound of the formula (2) with a reactive derivative (e.g., an acid halide, an acid anhydride, etc.) of the carboxylic acid of the formula (3).

The reaction is usually carried out in the presence of a base. The reaction is usually carried out in a solvent.

Examples of the base include organic bases such as triethylamine, pyridine, N,N-diethylaniline, 4-dimethylaminopyridine and diisopropylethylamine. The solvent to be used may be an inert solvent in the reaction, and examples thereof include hydrocarbons such as toluene and hexane; ethers such as diethyl ether and tetrahydrofuran; halogenated hydrocarbons such as chloroform, dichloromethane and 1,2-dichloroethane; and their mixtures.

The reaction time of the reaction is usually from an instant to 72 hours, and the reaction temperature is usually in the range from −20° C. to 100° C.

The amount of the alcohol compound of the formula (2) to be used in the reaction is theoretically 1 mol per 1 mol of the reactive derivative of the carboxylic acid of the formula (3), and however, usually, it can be appropriately selected in the range from 0.5 to 2.0 mol per 1 mol of the reactive derivative of the carboxylic acid of the formula (3). The amount of the base to be used in the reaction is usually 1 mol per 1 mol of the reactive derivative of the carboxylic acid of the formula (3), and however, it can be appropriately changed according to the reaction conditions.

After completion of the reaction, the present compound can be isolated by subjecting the reaction mixture to conventional after-treatment operations such as pouring into water, followed by extraction with an organic solvent and further concentration. If necessary, the present compound thus isolated can be purified by subjecting to a purification operation such as chromatography and distillation.

The alcohol compound of the formula (2) can be a compound described in JP-A 61-207361, or can be produced according to a process described in JP-A 61-207361.

The carboxylic acid of the formula (3) can be produced according to a process described in, for example, Agr. Biol. Chem., 37(10), 2241-2244 (1973), Agr. Biol. Chem., 31(10), 1143-1150 (1967) or JP-A 2001-302590. A reactive derivative of the carboxylic acid represented by the formula (3) can be produced from the carboxylic acid represented by the formula (3) by a conventional process.

Since the present compound has two asymmetric carbon atoms on the cyclopropane ring, the present compound has four isomers.

The four isomers, i.e., a (1R)-trans isomer, a (1S)-trans isomer, a (1R)-cis isomer and a (1S)-cis isomer, can be produced from the respective corresponding isomers of the carboxylic acid represented by the formula (3) (or a reactive derivative thereof).

Herein, the terms "(1R)" and "(1S)" denote positions on the cyclopropane ring and absolute configurations. The terms "trans" and "cis" mean relative configurations of substituents at the 1-position and the 3-position on the cyclopropane ring.

Examples of the pests on which the present compound exerts an effect include harmful arthropods such as harmful insects and ticks. Specific examples thereof are as follows.

Lepidoptera:

Pyralidae such as *Chilo suppressalis, Cnaphalocrocis medinalis* and *Plodia interpunctella*, Noctuidae such as *Spodoptera litura, Pseudaletia separate* and *Mamestra brassicae*, Pieridae such as *Pieris rapae crucivora*, Tortricidae such as *Adoxophyes* spp., Carposinidae, Lyonetiidae, Lymantriidae, *Autographa, Agrotis* spp. such as *Agrotis segetum* and *Agrotis ipsilon, Helicoverpa* spp., *Heliothis* spp., *Plutella xylostella, Parnara guttata, Tinea translucens, Tineola bisselliella*, etc.

Diptera:

*Culex* spp. such as *Culex pipiens pallens* and *Culex tritaeniorhynchus, Aedes* spp. such as *Aedes aegypti* and *Aedes albopictus, Anopheles* spp. such as *Anopheles sinensis*, Chironomidae, Muscidae such as *Musca domestica, Muscina stabulans* and *Fannia canicularis*, Calliphoridae, Sarcophagidae, Anthomyiidae such as *Delia platura* and *Delia antique*, Tephritidae, Agromyzidae, Drosophilidae, Psychodidae, Phoridae, Tabanidae, Simuliidae, Stomoxyidae, Ceratopogonidae, etc.

Blattaria:

*Blattella germanica, Periplaneta fuliginosa, Periplaneta americana, Periplaneta brunnea, Blatta orientalis*, etc.

Hymenoptera:

Formicidae, Vespidae, Bethylidae, Tenthredimidae such as *Athalia rosae ruficornis*, etc.

Siphonaptera:

*Ctenocephalides canis, Ctenocephalides felis, Pulex irritans*, etc.

Anoplura:

*Pediculus humanus, Pthirus pubis, Pediculus capitis, Pediculus corporis*, etc.

Isoptera:

*Reticulitermes speratus, Coptotermes formosanus*, etc.

Hemiptera:

Delphacidae such as *Laodelphax striatellus, Nilaparvata lugens* and *Sogatella furcifera*, Deltocephalidae such as *Nephotettix virescens* and *Nephotettix cincticeps*, Aphididae, Pentatomidae, Aleyrodidae, Coccoidea, Cimicidae such as *Cimex lectularius*, Tingidae, Psyllidae, etc.

Coleoptera:

*Attagenus unicolor japonicus, Authrenus verbasci*, Corn Rootworms such as *Diabrotica virgifera* and *Diabrotica undecimpunctata howardi*, Scarabaeidae such as *Anomala cuprea* and *Anomala rufocuprea*, Curculionidae such as *Sitophilus zeamais, Lissorhoptrus oryzophilus, Anthonomus grandis grandis* and *Callosobruchus chinensis*, Tenebrionidae such as *Tenebrio molitor* and *Tribolium castaneum*, Chrysomelidae such as *Oulema oryzae, Phyllotreta striolata* and *Aulacophora femoralis*, Anobiidae, *Epilachna* spp. such as *Epilachna vigintioctopunctata*, Lyctidae, Bostrychidae, Cerambycidae, *Paederus fuscipes*, etc.

Thysanoptera:

*Thrips palmi, Frankliniella occidentalis, Thrips hawaiiensis*, etc.

Orthoptera:

Gryllotalpidae, Acrididae, etc.

Acarina:

Pyroglyphidae such as *Dermatophagoides farinae* and *Dermatophagoides pteronyssinus*, Acaridae such as *Tyrophagus putrescentiae* and *Aleuroglyphus ovatus*, Glycyphagidae such as *Glycyphagus privatus, Glycyphagus domesticus* and *Glycyphagus destructor*, Cheyletidae such as *Cheyletus malaccensis* and *Cheyletus fortis*, Tarsonemidae, *Chortoglyphus* spp., Oribatei, Tetranychidae such as *Tetranychus urticae, Tetranychus kanzawai, Panonychus citri* and *Panonychus ulmi*, Ixodidae such as *Haemaphysalis longiconis*, Dermanyssidae such as *Ornithonyssus sylviarum* and *Dermanyssus gallinae*, etc.

The pest controlling composition of the present invention contains the present compound as an active ingredient.

The pest controlling composition of the present invention may be the present compound itself, or may be formulated into a form as described below.

Examples of the formulation form include an oil solution, an emulsifiable concentrate, a wettable powder, flowable formulation (e.g., an aqueous suspension, or an aqueous emulsion), a microcapsule, a dust, a granule, a tablet, an aerosol, a carbon dioxide formulation, a heat transpiration formulation (e.g., an insecticidal coil, an electric insecticidal mat, or a liquid absorbing core-type heat transpiration pesticide), a piezo insecticidal formulation, a heat fumigant (e.g., a self combustion-type fumigant, a chemical reaction-type fumigant, or a porous ceramic plate fumigant), an unheated transpiration formulation (e.g., a resin transpiration formulation, a paper transpiration formulation, an unwoven fabric transpiration formulation, a knit fabric transpiration formulation, or a sublimating tablet), an aerosol formulation (e.g., a fogging formulation), a direct contact formulation (e.g., a sheet-shaped contact formulation, a tape-shaped contact formulation, or a net-shaped contact formulation), an ULV formulation and a poison bait.

When the pest controlling composition of the present invention is in the form of a formulation, the formulation can be prepared, for example, by the following methods.

(1) A method comprising mixing the present compound with a solid carrier, a liquid carrier, a gaseous carrier or a poison bait, followed by addition of a surfactant and other auxiliary agents for formulation, and if necessary, further processing.

(2) A method comprising impregnation of a base material containing no active ingredient with the present compound.

(3) A method comprising mixing the present compound and a base material, followed by subjecting the mixture to mold processing.

When the pest controlling composition of the present invention is in the form of a formulation, the formulation contains usually 0.001 to 98% by weight of the present compound, depending on formulation forms.

Examples of the solid carrier for the formulation include fine powders or granules of clays (e.g., kaolin clay, diatomaceous earth, bentonite, Fubasami clay, or acid white clay), synthetic hydrated silicon oxide, talc, ceramics, other inorganic minerals (e.g., sericite, quartz, sulfur, active carbon, calcium carbonate, or hydrated silica) and chemical fertilizers (e.g., ammonium sulfate, ammonium phosphate, ammonium nitrate, ammonium chloride, or urea); substances that are solid at room temperature (e.g., 2,4,6-triisopropyl-1,3,5-trioxane, naphthalene, p-dichlorobenzene, or camphor, adamantine); and felt, fiber, fabric, knit, sheet, paper, thread, foam, porous material and multi-filament comprising one or more substances selected from the group consisting of wool, silk, cotton, hemp, pulp, synthetic resins (e.g., polyethylene resins such as low density polyethylene, straight chain low density polyethylene and high density polyethylene; ethylene-vinyl ester copolymers such as an ethylene-vinyl acetate copolymer; ethylene-methacrylate copolymers such as an ethylene-methyl methacrylate copolymer and an ethylene-ethyl methacrylate copolymer; ethylene-acrylate copolymers such as an ethylene-methyl acrylate copolymer and an ethylene-ethyl acrylate copolymer; ethylene-vinylcarboxylic acid copolymers such as an ethylene-acrylic acid copolymer; ethylene-tetracyclododecene copolymers; polypropylene resins such as a propylene homopolymer and a propylene-ethylene copolymer; poly-4-methylpentene-1, polybutene-1, polybutadiene, polystyrene; acrylonitrile-styrene resin; acrylonitrile-butadiene-styrene resins; styrene elastomers such as a styrene-conjugated diene block copolymer and a hydrogenated styrene-conjugated diene block copolymer; fluorine resins; acrylic resins such as methyl polymethacrylate; polyamide resins such as nylon 6 and nylon 66; polyester resins such as polyethylene terephthalate, polyethylene naphthalate, polybutylene terephthalate and polycyclohexylene dimethylene terephthalate; or porous resins such as polycarbonate, polyacetal, polyacryl sulfone, polyarylate, hydroxybenzoic acid polyester, polyetherimide, polyester carbonate, polyphenylene ether resins, polyvinyl chloride, polyvinylidene chloride, polyurethane, foamed polyurethane, foamed polypropylene and foamed ethylene), glass, metal and ceramics.

Examples of the liquid carrier include aromatic or aliphatic hydrocarbons (e.g., xylene, toluene, alkylnaphthalene, phenylxylylethane, kerosene, light oil, hexane, or cyclohexane), halogenated hydrocarbons (e.g., chlorobenzene, dichloromethane, dichloroethane, or trichloroethane), alcohols (e.g., methanol, ethanol, isopropyl alcohol, butanol, hexanol, benzyl alcohol, or ethylene glycol), ethers (e.g., diethyl ether, ethylene glycol dimethyl ether, diethylene glycol monomethyl ether, diethylene glycol monoethyl ether, propylene glycol monomethyl ether, tetrahydrofuran, or dioxane), esters (e.g., ethyl acetate, or butyl acetate), ketones (e.g., acetone, methyl ethyl ketone, methyl isobutyl ketone, or cyclohexanone), nitriles (e.g., acetonitrile, or isobutyronitrile), sulfoxides (e.g., dimethyl sulfoxide), acid amides (e.g., N,N-dimethylformamide, N,N-dimethylacetamide, or N-methylpyrrolidone), alkylidene carbonate (e.g., propylene carbonate), vegetable oils (e.g., soybean oil, or cottonseed oil), plant essential oils (e.g., orange oil, hyssop oil, or lemon oil), and water.

Examples of the gaseous carrier include butane gas, chlorofluorocarbon, liquefied petroleum gas (LPG), dimethyl ether and carbon dioxide.

Examples of the surfactant include alkyl sulfate, alkyl sulfonate, alkylaryl sulfonate, alkylaryl ethers, polyoxyethylenated alkylaryl ethers, polyethylene glycol ethers, polyhydric alcohol esters and sugar alcohol derivatives.

Examples of the other auxiliary agents for formulation include a binder, a dispersant and a stabilizer. Specifically, there are, for example, casein, gelatin, polysaccharides (e.g., starch, gum arabic, cellulose derivatives, or alginic acid), lignin derivatives, bentonite, saccharides, synthetic water-soluble polymers (e.g., polyvinyl alcohol, or polyvinyl pyrrolidone), polyacrylic acid, BHT (2,6-di-tert-butyl-4-methylphenol) and BHA (a mixture of 2-tert-butyl-4-methoxyphenol and 3-tert-butyl-4-methoxyphenol).

Examples of a base material for the insecticidal coil include a mixture of vegetable powder such as wood flour and lees powder, and a binder such as incense material powder, starch and gluten.

Examples of a base material for the electric insecticidal mat include a plate obtained by hardening cotton linter and a plate obtained by hardening fibrils of a mixture of cotton linter and pulp.

Examples of a base material for the self combustion-type fumigant include combustible exothermic agents such as nitrate, nitrite, guanidine salt, potassium chlorate, nitrocellulose, ethylcellulose and wood flour, thermal decomposition stimulants such as alkali metal salt, alkaline earth metal salt, dichromate and chromate, oxygen carriers such as potassium nitrate, combustion-supporting agents such as melamine and flour starch, extenders such as diatomaceous earth, and binders such as synthetic glue.

Examples of a base material for the chemical reaction-type fumigant include exothermic agents such as alkali metal sulfide, polysulfide, hydrosulfide and calcium oxide, catalytic agents such as a carbonaceous material, iron carbide and active white clay, organic foaming agents such as azodicarbonamide, benzenesulfonylhydrazide, dinitropentamethylenetetramine, polystyrene and polyurethane, and fillers such as strips of natural fiber and synthetic fiber.

Examples of a base material for the resin formulations such as resin transpiration formulations include polyethylene resins such as low density polyethylene, straight chain low density polyethylene and high density polyethylene; ethylene-vinyl ester copolymers such as an ethylene-vinyl acetate copolymer; ethylene-methacrylate copolymers such as an ethylene-methyl methacrylate copolymer and an ethylene-ethyl methacrylate copolymer; ethylene-acrylate copolymers such as an ethylene-methyl acrylate copolymer and an ethylene-ethyl acrylate copolymer; ethylene-vinylcarboxylic acid copolymers such as an ethylene-acrylic acid copolymer; ethylene-tetracyclododecene copolymers; polypropylene resins such as a propylene copolymer and a propylene-ethylene copolymer; poly-4-methylpentene-1, polybutene-1, polybutadiene, polystyrene, acrylonitrile-styrene resins; acrylonitrile-butadiene-styrene resins; styrene elastomers such as a styrene-conjugated diene block copolymer and a hydrogenated styrene-conjugated diene block copolymer; fluorine resins; acrylic resins such as methyl polymethacrylate; polyamide resins such as nylon 6 and nylon 66; polyester resins such as polyethylene terephthalate, polyethylene naphthalate, polybutylene terephthalate and polycyclohexylene dimethylene terephthalate; polycarbonate, polyacetal, polyacryl sulfone, polyarylate, hydroxybenzoic acid polyester, polyetherimide, polyester carbonate, polyphenylene ether resin, polyvinyl chloride, polyvinylidene chloride and polyurethane.

These base materials may be used alone or as a combination of two or more kinds. If necessary, a plasticizer such as phthalate (e.g., dimethyl phthalate, dioctyl phthalate, etc.), adipic acid esters and stearic acid may be added to these base materials.

The resin formulation can be prepared by mixing the present compound with the base material, kneading the mixture, followed by molding it by injection molding, extrusion molding or pressure molding.

The resultant resin formulation can be subjected to further molding or cutting procedure, if necessary, to be processed into a plate, film, tape, net or string shape. These resin formulations can be processed into animal collars, animal ear tags, sheet products, trap strings, gardening supports and other products.

Examples of a base material for the poison bait include food ingredients such as grain powder, vegetable oil, saccharide and crystalline cellulose, antioxidants such as dibutylhydroxytoluene and nordihydroguaiaretic acid, preservatives such as dehydroacetic acid, accidental ingestion inhibitors for children and pets such as a chili powder; insect attraction fragrances such as cheese flavor, onion flavor and peanut oil.

The pest controlling method of the present invention comprises applying an effective amount of the present compound to a pest or a habitat thereof.

The pest controlling method of the present invention is carried out by applying an effective amount of the present compound, usually in the form of a formulation, to a pest or a habitat thereof.

A method for applying the present compound is not particularly limited, and appropriately selected depending on the form of the composition, the application area and the like.

Examples of the application method include the following methods.

(1) A method comprising applying a formulation of the present compound as it is to a pest or a habitat of the pest.

(2) A method comprising diluting a formulation of the present compound with a solvent such as water, and then spraying the dilution to a pest or a habitat of the pest.

In this method, the present compound is usually formulated into an emulsifiable concentrate, a wettable powder, a flowable formulation, a microcapsule or the like. The formulation is usually diluted so that the concentration of the present compound can be 0.1 to 10,000 ppm before spraying.

(3) A method comprising heating or placing a formulation of the present compound at a habitat of a pest, thereby allowing the present compound to volatilize and diffuse from the composition.

For example, when the present compound is formulated into an insecticidal coil or an electric insecticidal mat, the present compound can be volatilized and diffused by heating the formulation.

When the present compound is formulated into a resin transpiration formulation, a paper transpiration formulation, an unwoven fabric transpiration formulation, a knit fabric transpiration formulation or a sublimating tablet, the present compound can be volatilized and diffused by placing the formulation in a space to be pest-controlled with or without air blowing.

The controlling method of the present invention can be performed for the purpose of prevention of epidemics and external parasite control.

The habitat of a pest is not particularly limited, as long as it is a place where the pest inhabits. The habitat may be a space, or a plane such as floor and ground.

In the case where the present compound is applied for the purpose of prevention of epidemics, examples of the habitat of a pest include a closet, a Japanese cabinet, a Japanese chest, a cupboard, a toilet, a bathroom, a shed, a living room, a dining room, a garage and the interior of a car. The present compound can be also applied to outdoor open space.

In the controlling method of the present invention, the amount and concentration of the present compound to be applied can be appropriately determined depending on the form, application period, application area, application method, kind of a pest, damage to be incurred and other factors.

When the pest controlling composition of the present invention is used for prevention of epidemics, the amount to be applied is usually from 0.0001 to 1000 mg/m$^3$ of the present compound in the case of applying to a space, and from 0.0001 to 1,000 mg/m$^2$ of the present compound in the case of applying to a plane.

When the present compound is used for controlling external parasites of livestock such as cows, horses, pigs, sheep, goats and chickens and small animals such as dogs, cats, rats and mice, the pest controlling composition of the present invention can be applied to the animals by a known method in the veterinary field. Specifically, when systemic control is intended, the pest controlling composition of the present invention is administered to the animals as a tablet, a mixture with feed or a suppository, or by injection (including intramuscular, subcutaneous, intravenous and intraperitoneal injections). On the other hand, when non-systemic control is intended, the pest controlling composition of the present invention is applied to the animals by means of spraying of the oil solution or aqueous solution, pour-on or spot-on treatment, or washing of the animal with a shampoo formulation, or by putting a collar or ear tag made of the resin transpiration formulation to the animal. The dosage of the present compound is usually in the range from 0.1 to 1000 mg per 1 kg of an animal body weight.

The present compound can be used as a mixture or in combination with one or more other insecticides, acaricides, nematocides, soil pest controlling agents, fungicides, herbicides, repellents and/or synergists.

Examples of the active ingredient for the insecticide and the acaricide include:

organic phosphorous compounds such as dichlorvos, fenitrothion, cyanophos, profenofos, sulprofos, phenthoate, isoxathion, tetrachlorvinphos, fenthion, chlorpyrifos, diazinon, acephate, terbufos, phorate, chlorethoxyfos, fosthiazate, ethoprophos, cadusafos, methidathion, disulfoton, dioxabenzofos, dimethoate, phenthoate, malathion, trichlorphon, azinphos-methyl, monocrotophos, ethion, etc.;

carbamate compounds such as propoxur, carbaryl, metoxadiazone, fenobucarb, methomyl, thiodicarb, alanycarb, benfuracarb, oxamyl, aldicarb, methiocarb, carbosulfan, ethiofencarb, fenothiocarb, cartap, etc.;

pyrethroid compounds such as allethrin, tetralomethrin, prallethrin, d-phenothrin, d-resmethrin, cyphenothrin, permethrin, cypermethrin, alpha-cypermethrin, zeta-cypermethrin, deltamethrin, tralomethrin, cyfluthrin, beta-cyfluthrin, cyhalothrin, lambda-cyhalothrin, d-furamethrin, imiprothrin, ethofenprox, fenvalerate, esfenvalerate, fenpropathrin, silafluofen, bifenthrin, transfluthrin, flucythrinate, tau-fluvalinate, acrinathrin, tefluthrin, cycloprothrin, metofluthrin, profluthrin, dimefluthrin, empenthrin, flumethrin, fluvalinate, 2-methyl-2-(4-bromodifluoromethoxyphenyl)propyl (3-phenoxybenzyl)ether, and 5-(2-propynyl)furfuryl 2,2,3,3-tetramethylcyclopropane carboxylate;

neonicotinoid compounds such as acetamiprid, nitenpyram, thiacloprid, thiamethoxam, dinotefuran, clothianidine, imidacloprid, etc.;

chlorinated hydrocarbon compounds such as endosulfan, γ-BHC, 1,1-bis(chlorophenyl)-2,2,2-trichloroethanol, etc.;

benzoylphenyl urea compounds such as lufenuron, chlorfluazuron, hexaflumuron, diflubenzuron, triflumuron, teflubenzuron, flufenoxuron, fluazuron, novaluron, triazuron, bistrifluoron, flufenoxuron, etc.;

juvenile hormone analogues such as pyriproxyfen, methoprene, hydroprene, phenoxycarb, etc.;

phenylpyrazole compounds such as acetoprole, pyriprole, pyrafluprole, ethiprole, etc.;

benzoylhydrazine compounds such as tebufenozide, chromafenozide, methoxyfenozide, halofenozide, etc.;

macrolide compounds such as polynactin complex (tetranactin, dinactin and trinactin), abamectin, emamectin benzoate, spinosad, ivermectin, azadirachtin, milbemectin, etc.; and diafenthiuron, pymetrozine, flonicamide, triazamate, buprofezin, spinosad, emamectin benzoate, chlorphenapyr, indoxacarb MP, pyridalyl, cyromazine, fenpyroximate, tebufenpyrad, tolefenpyrad, pyridaben, pyrimidifen, fluacrypyrim, etoxazole, fenazaquin, acequinocyl, hexythiazox, clofentezine, fenbutatin oxide, dicofol, propargite, abamectin, avermectin, milbemectin, amitraz, bensultap, thiocyclam, endosulfan, spirodiclofen, spiromesifen, amidoflumet and azadirachtin, bromopropylate, tetradifon, chinomethionat, polynactin complex (tetranactin, dinactin and trinactin), abamectin, metaflumizon, flubendiamide, chlorantraniliprole and pyrifluquinazon.

Examples of the active ingredient of the repellent include 3,4-caranediol, N,N-diethyl-m-toluamide, 1-methylpropyl 2-(2-hydroxyethyl)-1-piperidine carboxylate, p-menthane-3,8-diol and vegetable essential oils such as a hyssop oil.

Examples of the active ingredient of the synergist include bis-(2,3,3,3-tetrachloropropyl)ether (S-421), N-(2-ethylhexyl)bicyclo[2.2.1]hept-5-ene-2,3-dicarboxylmide (MGK-264) and α-[2-(2-butoxyethoxy)ethoxy]-4,5-methylenedioxy-2-propyltoluene (piperonyl butoxide).

Examples of the nematocides, the soil pest controlling agents, the fungicides and the herbicides include conventionally known ones.

EXAMPLES

The present invention will be described in more detail by way of Production Examples, Formulation Examples and Test Examples which the present invention is not limited to.

First, a production example of the present compound will be described.

Production Example 1

To a mixture solution of 55 mg (0.25 mmol) of 4-(2-propynyl)-2,3,5,6-tetrafluorobenzylalcohol, 22 mg (0.27 mmol) of pyridine and 3 mL of tetrahydrofuran was added 37 mg (0.25 mmol) of (1R)-trans-2,2,3-trimethylcyclopropanecarboxylic acid chloride under ice cooling, and the mixture was stirred at room temperature for 8 hours.

The reaction mixture was poured into 10 ml of iced water and then extracted twice with 20 ml of ethyl acetate. The organic layers were combined, washed with a saturated aqueous sodium chloride solution, dried over magnesium sulfate and then concentrated under reduced pressure. The residue was subjected to silica gel column chromatography (product name: Silica Gel 60N (spheerical and neutral), manufactured by Kanto Chemical Co., Inc.) to obtain 70 mg of 4-(2-propynyl)-2,3,5,6-tetrafluorobenzyl (1R)-trans-2,2,3-trimethylcyclopropanecarboxylate represented by the following formula:

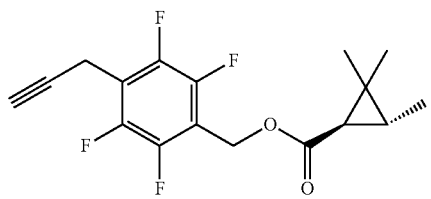

(hereinafter referred to as the present compound (1)) as a clear colorless liquid (yield: 84%).

$^1$HNMR (CDCl$_3$) δ (ppm): 1.10 (3H, d), 1.15 (3H, s), 1.21 (3H, s), 1.82 (1H, m), 1.88 (1H, m), 2.07 (1H, brt), 3.63 (2H, brs), 5.20 (2H, s).

Formulation Examples will be described hereinafter. All the parts represent amounts by mass.

Formulation Example 1

An emulsifiable concentration is obtained by dissolving 20 parts of the present compound (1) in 65 parts of xylene, adding 15 parts of Sorpol 3005X (registered trade name of Toho Chemical Co., Ltd.) thereto, and thoroughly mixing the mixture with stirring.

Formulation Example 2

A wettable powder is obtained by adding 5 parts of Sorpol 3005X to 40 parts of the present compound (1), thoroughly mixing the mixture, adding 32 parts of Carplex #80 (synthetic hydrated silicon oxide, registered trade name of Sionogi Pharmaceutical Co., Ltd.) and 23 parts of 300 mesh diatomaceous earth thereto, and mixing the mixture with stirring by a juice mixer.

Formulation Example 3

A mixture of 1.5 parts of the present compound (1), 1 part of Tokuseal GUN (synthetic hydrated silicon oxide, manufactured by Tokuyama Corp.), 2 parts of Reax 85A (sodium ligninsulfonate, manufactured by West Vaco Chemicals), 30 parts of Bentonite Fuji (bentonite, manufactured by Hojun Corp.) and 65.5 parts of Shokozan A clay (kaolin clay, manufactured by Shokozan Kogyosho) are thoroughly ground, and water is added thereto. The mixture is then thoroughly kneaded, granulated with an extrusion granulator, and dried to obtain a 1.5% granule.

Formulation Example 4

A mixture of 10 parts of the present compound (1), 10 parts of phenylxylylethane and 0.5 part of Sumijul L-75 (tolylene diisocyanate, manufactured by Sumitomo Bayer Urethane Ltd.) is added to 20 parts of a 10% aqueous solution of gum arabic, followed by stirring with a homomixer to obtain an emulsion having a mean particle diameter of 20 λm. The emulsion is further mixed with 2 parts of ethylene glycol and the mixture is stirred in a warm bath at 60° C. for 24 hours to obtain microcapsule slurry. Separately, a thickening agent solution is prepared by dispersing 0.2 part of xanthan gum and 1.0 part of Veegum R (aluminum magnesium silicate, manufactured by Sanyo Chemical) in 56.3 parts of ion-exchanged water. A microcapsule formulation is obtained by mixing 42.5 parts of the microcapsule slurry and 57.5 parts of the thickening agent solution.

Formulation Example 5

A mixture of 10 parts of the present compound (1) and 10 parts of phenylxylylethane is added to 20 parts of a 10% aqueous solution of polyethylene glycol, followed by stirring with a homomixer to obtain an emulsion having a mean particle diameter of 3 μm. Separately, a thickening agent solution is prepared by dispersing 0.2 part of xanthan gum and 1.0 part of Veegum R (aluminum magnesium silicate, manufactured by Sanyo Chemical) in 58.8 parts of ion-exchanged water. A flowable formulation is obtained by mixing 40 parts of the above emulsion and 60 parts of the thickening agent solution.

Formulation Example 6

A dust is obtained by mixing 5 parts of the present compound (1), 3 parts of Carplex #80 (synthetic hydrated silicon oxide, registered trade name of Sionogi Pharmaceutical Co., Ltd.), 0.3 part of PAP (a mixture of monoisopropyl phosphate and diisopropyl phosphate) and 91.7 parts of talc (300 mesh) with stirring by a juice mixer.

Formulation Example 7

An oil solution is obtained by dissolving 0.1 part of the present compound (1) in 10 parts of dichloromethane, and mixing the solution with 89.9 parts of deodorized kerosene.

Formulation Example 8

An oil aerosol is obtained by mixing and dissolving 1 part of the present compound (1), 5 parts of dichloromethane and 34 parts of deodorized kerosene, filling an aerosol vessel with the resultant solution, attaching a valve to the vessel, and charging the vessel with 60 parts of a propellent (liquefied petroleum gas) under pressure through the valve.

Formulation Example 9

An aqueous aerosol is obtained by mixing and dissolving 0.6 part of the present compound (1), 5 parts of xylene, 3.4 parts of deodorized kerosene and 1 part of sorbitan monolaurate (Leodor SP-L10, manufactured by Kao Co., Ltd., HLB: 8.6), filling an aerosol vessel with the resultant solution and 50 parts of water, attaching a valve to the vessel, and charging the vessel with 40 parts of a propellent (liquefied petroleum gas) under pressure through the valve.

Formulation Example 10

An insecticidal coil is obtained by dissolving 0.3 g of the present compound (1) in 20 mL of acetone, uniformly mixing and stirring the solution and 99.7 g of a base material for an insecticidal coil (a mixture of an incense material powder, lees flour and wood flour in a ratio of 4:3:3), adding 100 mL of water thereto, thoroughly kneading the mixture, and molding and drying the mixture.

Formulation Example 11

An electric insecticidal mat is obtained by dissolving 0.8 g of the present compound (1) and 0.4 g of piperonyl butoxide in acetone to obtain 10 mL of the solution, and uniformly impregnating, with 0.5 mL of the solution, a base material (in a plate form, obtained by hardening fibrils comprised of a mixture of cotton linter and pulp) for an electric insecticidal mat of 2.5 cm×1.5 cm and 0.3 cm thick.

Formulation Example 12

A part to be used for a liquid absorbing core-type heat transpiration device is obtained by dissolving 3 parts of the present compound (1) in 97 parts of deodorized kerosene, placing the resultant solution in a vessel made of vinyl chloride, and inserting a liquid-absorbing core into the vessel. The liquid-absorbing core is prepared by solidifying an inorganic powder with a binder, followed by sintering it, upper part of which can be heated by a heater.

Formulation Example 13

A heat fumigant is obtained by dissolving 100 mg of the present compound (1) in an appropriate amount of acetone, and impregnating a porous ceramic plate of 4.0 cm×4.0 cm and 1.2 cm thick with the solution.

Formulation Example 14

A room-temperature-volatilizing formulation is obtained by dissolving 100 μg of the present compound (1) in an appropriate amount of acetone, uniformly applying the solution onto a filter paper of 2 cm×2 cm and 0.3 mm thick, and air-drying to remove acetone.

The following Test Examples show that the present compound is effective as an active ingredient of a pest controlling composition.

In Test Examples, 4-methoxymethyl-2,3,5,6-tetrafluorobenzyl (1R)-trans-2,3,3-trimethylcyclopropanecarboxylate represented by the following formula:

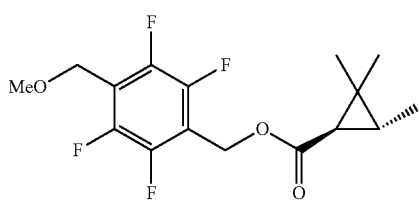

(a compound described in JP-A 2001-302590, hereinafter referred to as the comparative compound (B)) was used as a comparative control compound.

Test Example 1

A 0.005% (w/v) solution of a test compound in acetone was prepared. The nota of 10 female imagoes of *Culex pipiens pallens* were treated with the acetone solution in an amount of 0.015 μg of the test compound per mosquito. Then, water and feed were given to the test mosquitoes. After 24 hours, the number of dead mosquitoes was counted, and a death rate was calculated (2 repetitions).

The results are shown in Table 1.

TABLE 1

| Test compound | Death rate (%) |
|---|---|
| Present compound (1) | 95 |
| Comparative compound (B) | 55 |

Test Example 2

A 0.002% (w/v) solution of a test compound in acetone was prepared. Then, 0.64 ml of the acetone solution was dropped onto the bottom of an aluminum dish having a diameter of 9 cm. Then, acetone was air-dried (drug amount: about 2 mg per 1 m$^2$). Ten female imagos of *Culex pipiens pallens* were released in a polyethylene cup (diameter: 9 cm; height: 4.5 cm), and the upper opening portion of the polyethylene cup was covered with a 16 mesh nylon net. Next, the cup was inverted onto the aluminum dish. After 60 minutes, the number of knocked down mosquitoes was counted and a knockdown rate was calculated (2 repetitions). As a result, the knockdown rate of the present compound (1) was 70%.

INDUSTRIAL APPLICABILITY

The present compound has an excellent pest controlling effect, and therefore it is useful as an active ingredient of a pest controlling composition.

The invention claimed is:

1. A cyclopropanecarboxylate represented by the formula (1):

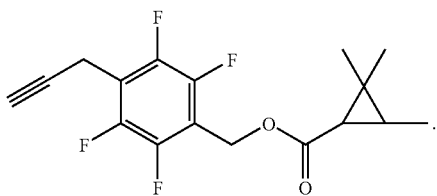

2. A pest controlling composition, which comprises the cyclopropanecarboxylate according to claim 1 as an active ingredient.

3. A pest controlling method, which comprises applying an effective amount of the cyclopropanecarboxylate according to claim 1 to a pest or a habitat of the pest.

* * * * *